United States Patent

Kapmeyer et al.

[11] Patent Number: 5,232,981
[45] Date of Patent: Aug. 3, 1993

[54] DISPERSION POLYMERS, A PROCESS FOR THE PREPARATION THEREOF, AND THE USE THEREOF

[75] Inventors: Wolfgang Kapmeyer; Michael Dengler, both of Marburg, Fed. Rep. of Germany

[73] Assignee: Behringwerke Aktiengesellschaft, Marburg/Lahn, Fed. Rep. of Germany

[21] Appl. No.: 499,553

[22] Filed: Mar. 26, 1990

Related U.S. Application Data

[63] Continuation of Ser. No. 242,674, Sep. 9, 1988, abandoned.

[30] Foreign Application Priority Data

Sep. 11, 1987 [DE] Fed. Rep. of Germany ....... 3730515

[51] Int. Cl.$^5$ .............................................. C08L 39/00
[52] U.S. Cl. ..................................... 524/555; 526/304
[58] Field of Search ........................... 424/78; 524/555; 526/304

[56] References Cited

U.S. PATENT DOCUMENTS 4,448,908  5/1984  Pauly et al. ..................... 523/201

FOREIGN PATENT DOCUMENTS 0080614  6/1982  European Pat. Off. .
0218827  4/1987  European Pat. Off. .

Primary Examiner—Paul R. Michl
Assistant Examiner—LaVonda DeWitt
Attorney, Agent, or Firm—Finnegan, Henderson, Farabow, Garrett & Dunner

[57] ABSTRACT

Dispersion polymers composed of a compound or of several compounds of the formula I $$CH_2=CR_1-CO-NH-(CH_2)_n-CH(OR_2)OR_3 \qquad I$$

in which
n is 1–6, and
$R_1$ is H or $CH_3$ and $R_2$ and $R_3$ are identical or different and denote $-(CH_2)_m-CH_3$ with m denoting 0–7 or $-C(X)(Y)Z$ with X, Y and Z denoting $(CH_2)_pCH_3$, and p denoting 1–3, where X, Y and Z can be identical or different, and, where appropriate, of another vinyl derivative or of other vinyl derivatives in an aqueous medium, a process for the preparation thereof, and the use thereof for the preparation of conjugates with biologically active substances are described.

13 Claims, 3 Drawing Sheets

DISPERSION POLYMERS, A PROCESS FOR THE PREPARATION THEREOF, AND THE USE THEREOF

This application is a continuation of application Ser. No. 07/242,674 filed Sep. 9, 1988 now abandoned.

The invention relates to dispersion polymers composed of latex particles which are a polymer of vinyl monomers which have an acetal group or have a copolymer of such monomers with other vinyl monomers, and to a process for the preparation thereof. These polymers can be used, by binding to them biologically active substances having free amino groups, for the preparation of biologically active latex conjugates suitable for serological or immunological determination methods.

It is known to increase the sensitivity of serological or immunological determination methods by use of indicator or carrier particles loaded with the appropriate immunological reagent. Latex particles with a diameter of 0.02 to 5 μm can be used as carrier particles.

European Patent Application EP-A 0,080,614 (U.S. Pat. No. 4,448,908) discloses latex particles which contain acetal groups bonded via amide groups. Latex cores previously prepared in an aqueous medium are swollen with vinyl monomers which contain acetal groups bonded via amide groups. These vinyl monomers, which must be sufficiently insoluble in water, are then copolymerized together with other monomers which can be hydrophilic or ionic in nature. Reagents of this type can be employed for nephelometric determinations of serum proteins, for example of C-reactive protein.

The process described in EP-A 0,080,614 is elaborate because the latex particles are prepared in two stages, with cores being prepared first. In addition, the swelling of the cores for the shell polymerization takes place not with all vinyl monomers but only with those which are sufficiently insoluble in water.

Furthermore, the current core-shell polymerization process results only in latex particles of particular sizes, starting from available latex cores.

Hence there has been a need for a one-stage copolymerization process for the preparation of dispersion polymers of any desired size using vinyl compounds having acetal groups.

It has now been found, surprisingly, that the abovementioned disadvantages of the state of the art can be overcome by using carrier particles prepared by polymerization in an aqueous medium of acrylic or methacrylic monomers which contain acetal groups bonded via amide groups, together with other vinyl monomers.

Thus the invention relates to a dispersion polymer composed of a compound or of several compounds of the formula I

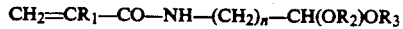

$$CH_2=CR_1-CO-NH-(CH_2)_n-CH(OR_2)OR_3 \qquad I$$

in which
n is 1–6, and $R_1$ is H or $CH_3$ and
$R_2$ and $R_3$ are identical or different and denote $-(CH_2)_m-CH_3$ with m denoting 0–7 or $-C(X)(Y)Z$ with X, Y and Z denoting $(CH_2)_pCH_3$, and p denoting 1–3, where X, Y and Z can be identical or different, and, where appropriate, of another vinyl derivative or of other vinyl derivatives in an aqueous medium.

Figure 1:
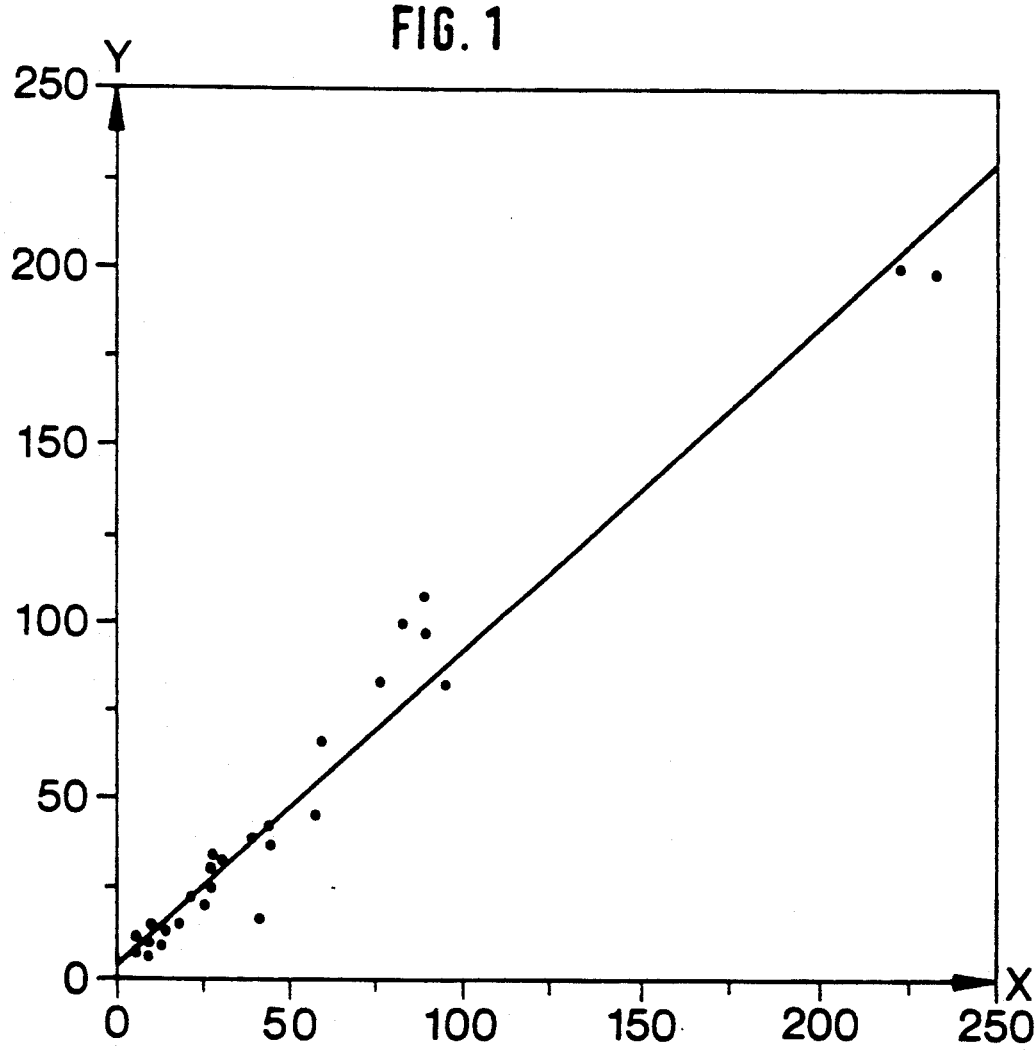
FIG. 1 is a plot of the results of CRP determinations using a polymer according to the invention in a turbidimetric assay (abscissa) in comparison with the classical nephelometric assay on the BNA system (NA-latex-CRP assay, Behringwerke AG) on the ordinate.

The compound of the formula I which is preferably used is acryl- or methacrylamidoalkanal dialkyl acetal with $C_2$- to $C_8$-alkyl in the acetal moiety. Particularly suitable acryl- or methacrylamidoacetaldehyde di-n-pentyl acetal.

Examples of suitable vinyl polymers not embraced by the formula I are styrene, vinylnaphthalene, vinyltoluene, methacrylic acid, acrylic acid or crotonic acid.

It is also advantageous to use additionally water-soluble monomers from the group comprising hydroxyl-substituted acrylic or methacrylic esters or amides such as, for example, N-(2,3-dihydroxypropyl)methacrylamide, N-(2-hydroxypropyl)methacrylamide or 2-hydroxypropyl methacrylate. It may also be advantageous to use additionally water-soluble monomers with a betaine structure such as, for example, N-(3-sulfopropyl)-N-methacryloxyethyl-N,N-dimethylammonium betaine or N-(3-sulfopropyl)-N-methacrylamidopropyl-N,N-dimethylammonium betaine.

The dispersions ("latices") according to the invention can be prepared by polymerization or, where appropriate, copolymerization of one or more vinyl monomers of the formula I and, where appropriate, other vinyl monomers in the presence of ionic and/or non-ionic detergents.

The invention therefore also relates to a process for the preparation of a polymer as defined above, which comprises a compound or several compounds of the formula I and, where appropriate, another vinyl derivative or other vinyl derivatives being polymerized in an aqueous medium in the presence of an emulsifier and of a radical-forming initiator.

Examples of suitable emulsifiers (detergents) are polyglycol ethers with long-chain aliphatic alcohols, which preferably have 10–20 carbon atoms, or alkylphenols whose alkyl radical preferably contains 6–12 carbon atoms, or dialkylphenols or trialkylphenols whose alkyl radicals are preferably branched alkyl radicals each having 3–12 carbon atoms. Examples of these are the products of the reaction of ethylene oxide with lauryl alcohol, stearyl alcohol, oleyl alcohol, coconut fatty alcohol, octylphenol, nonylphenol, diisopropylphenol, triisopropylphenol, di-t-butylphenol and tri-t-butylphenol. Products of the reaction of ethylene oxide with polypropylene glycol or polybutylene glycol are likewise suitable.

Of the ionic emulsifiers, particularly suitable are anionic emulsifiers, especially alkali metal or ammonium salts of alkylsulfonates, aylsulfonates or alkylarylsulfonates, as well as of the appropriate sulfates, phosphates or phosphonates, which optionally have oxyethylene units between the particular hydrocarbon radical and the anionic group. Examples of these are sodium dodecyl sulfate, sodium lauryl sulfate, sodium octylphenol glycol ether sulfate, sodium dodecylbenzenesulfonate, sodium lauryl diglycol sulfate, ammonium tri-t-butylphenol pentaglycol sulfate and ammonium tri-t-butylphenol octaglycol sulfate. A mixture of sodium dodecyl sulfate and octylphenoxypolyethoxyethanol (®Triton X405) is preferably used.

It is advantageous for up to 20% by weight, based on the monomer mixture, of dimethylformamide or other substances which reduce the viscosity to be added to the mixture composed of the monomers.

The polymerization or copolymerization can be carried out by processes customary per se. However, the preferred embodiment of the process according to the invention is the metering process in which the monomer or the monomer mixture is added dropwise, with continuous stirring, to the aqueous solution of emulsifier and the radical-forming initiator under polymerization conditions, i.e. at a temperature of $+10°$ C. to $+120°$ C., preferably $+50°$ C. to $+90°$ C.

Subsequently excess monomers and residues of initiator and emulsifier are removed from the polymer by known processes. It is advantageous to subject the polymer to dialysis, for example against $NaHCO_3$ buffer (0.01 to 0.05% by weight).

The invention additionally relates to the use of a polymer or copolymer according to the invention for preparing a conjugate with a biologically active substance.

To prepare a conjugate dispersion of this type, also called latex conjugate hereinafter, it is possible to adjust the pH of a suspension of the seed-polymerized latex particles described above to a value below 5, preferably below 3, and to incubate it with the immunologically active material which is to be bound, such as, for example, an antibody or antigen. The labile bonds between an amino group of the protein and the liberated aldehyde on the latex particle according to the invention are reduced by known processes. A solution of sodium cyanoborohydride in a neutral buffer is preferably used for this. Any unbound immunologically active material or other impurities are removed from the reaction mixture. This is expediently carried out by centrifugation or washing on suitable membranes.

The seed-polymerized latices according to the invention are distinguished by high stability. They are suitable for preparing especially sensitive reagents. This is important because the disadvantages of conventional reagents are evident, inter alia, from the fact that the results of nephelometric or turbidimetric measurements carried out with them do not agree well with those of an enzyme immunoassay. A reagent for determining C-reactive protein (CRP) has been prepared as in Examples 1 and 2. Turbidimetric measurements with this reagent were carried out as in Example 3.

The CRP reagent makes possible measurements between about 5 and 250 mg/l CRP. Thus, the diagnostically important range of measurement is completely covered. As is evident from FIG. 1, there is good agreement with the results of the nephelometric assay (Na-latex-CRP reagent, Behringwerke AG). The correlation constants are: Y (turbidimetry) $=0.909$ $\times$(BNA)$+5.821$ mg/l, r$=0.967$. Using the polymers according to the invention it is also possible to prepare reagents for trace protein measurements.

Figure 2:
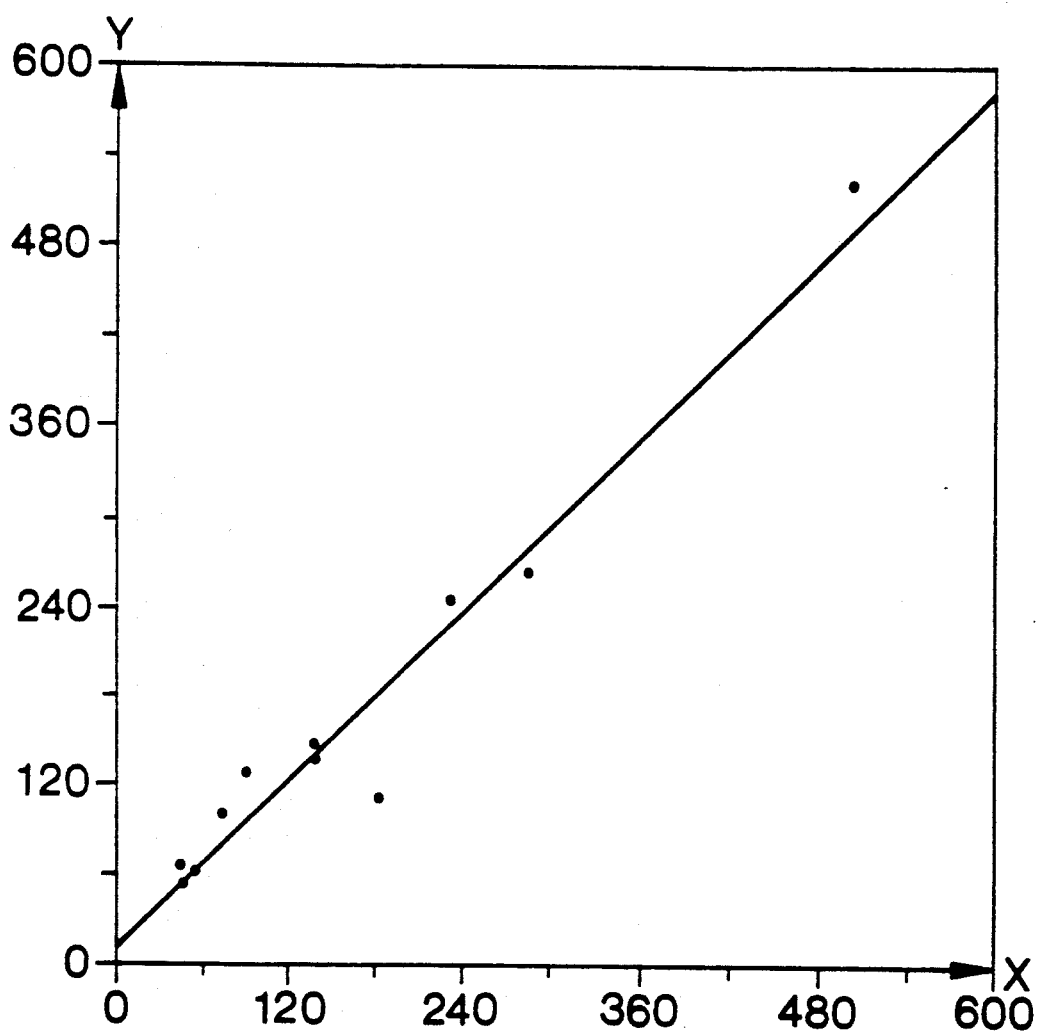
FIG. 2 shows the results of IgE measurements using a polymer according to the invention in a turbidimetric assay (abscissa) and the classical enzyme immunoassay (®Enzygnost IgE, Behringwerke AG) on the ordinate.

A reagent for the turbidimetric determination of immunoglobulin E (IgE) has been prepared as in Example 4, and a reagent for the turbidimetric determination of alpha-fetoprotein (AFP) has been prepared as in Example 6. The turbidimetric measurement of IgE was carried out as in Example 5, and the turbidimetric measurement of AFP was carried out as in Example 7. The range of measurement for the IgE reagent is between 30 and 2,000 IU/ml. There is good agreement for pooled sera with the results of the enzyme immunoassay (Enzygnost IgE, Behringwerke AG), as shown in FIG. 2. The correlation constants are: Y (turbidimetry) $=0.962$ $\times$(EIA)$+11.69$ IU/ml, r$=0.973$.

Figure 3:
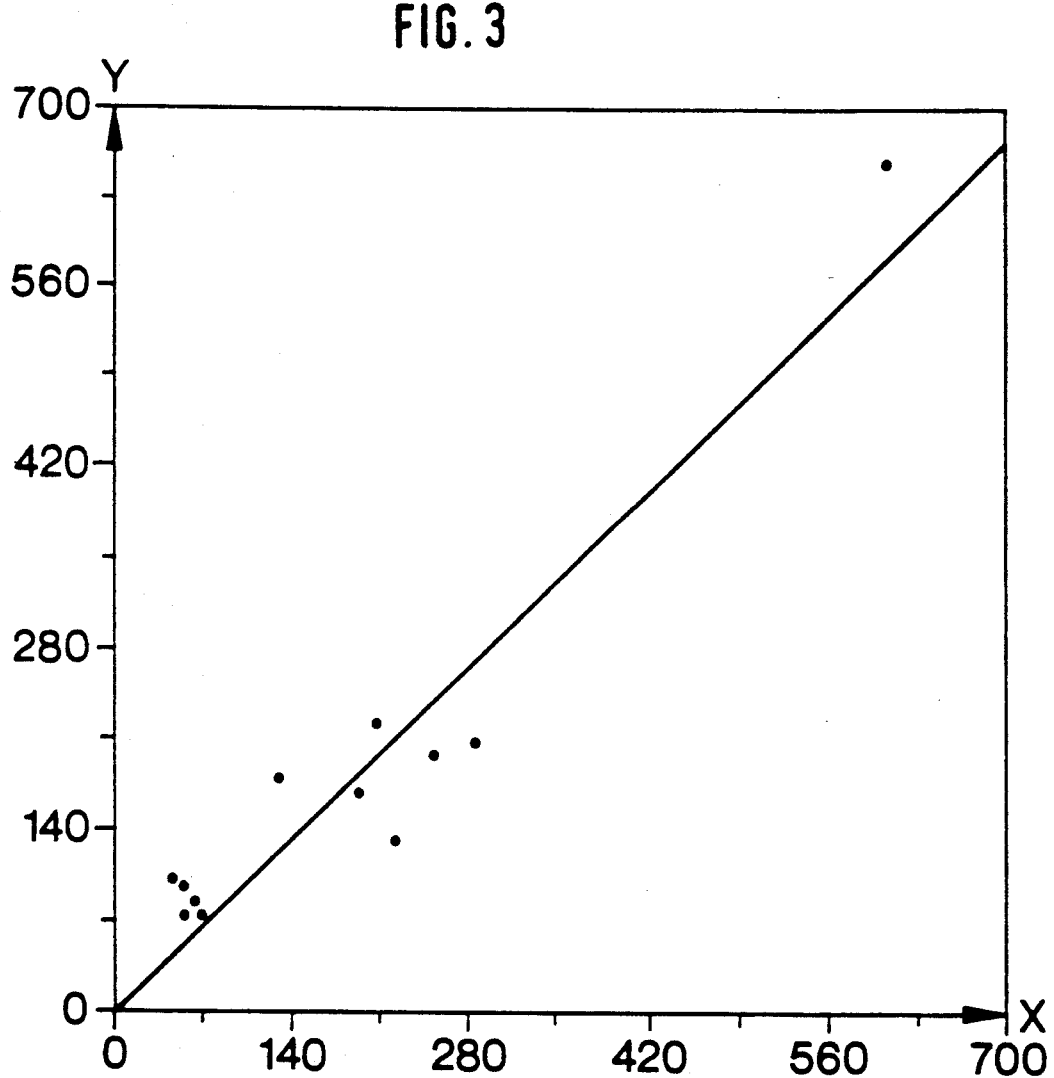
FIG. 3 depicts the results of AFP measurements using a polymer according to the invention in a turbidimetric assay (abscissa) and the classical enzyme immunoassay (®Enzygnost IgE, Behringwerke AG) on the ordinate.

The range of measurement for the AFP reagent is between 50 and 1,500 ng/ml. Satisfactory agreement was found for serum and plasma samples with the results of the enzyme immunoassay (Enzygnost AFP, Behringwerke AG), as shown in FIG. 3. The correlation constants are: Y (turbidimetry) $=0.965$ $\times$(EIA)$+4.31$ ng/ml, r$=0.945$.

The latex conjugates can be employed in all diagnostic methods which measure changes in particle size, for example in qualitative and semiquantitative determinations of substances with the aid of visual latex-agglutination tests, as well as in nephelometric or turbidimetric determinations of trace proteins in a direct or competitive agglutination test or in a latex-hapten inhibition test.

The examples which follow illustrate the invention.

EXAMPLE 1

Seed Polymer 77 ml of distilled water ($N_2$-saturated) were placed together with 2 mg of octylphenoxypolyethoxyethanol (®Triton $\times$405, dissolved in 2 ml of distilled water) and 50 mg of sodium dodecyl sulfate in the polymerization vessel, and the oxygen was removed. 1 ml of a potassium peroxydisulfate solution, 16 mg/ml in distilled water, was also added. A mixture of 0.4 ml of styrene, 0.4 ml of methacrylamidoacetaldehyde di-n-pentyl acetal and 0.002 ml of methacrylic acid was prepared.

The mixture of the monomers was slowly added dropwise, in 60 minutes, to the vigorously stirred aqueous solution at 70° C. The mixture was then stirred at the same temperature for a further 5 hours. After the mixture had been cooled to room temperature and filtered through a fluted filter, 78 ml of the polymer were obtained. It was subsequently dialyzed against $NaHCO_3$ buffer (0.25 g/l, pH 8–8.2) for about 20 hours. 80 ml of a latex suspension with a solids content of 0.71% by weight were obtained.

EXAMPLE 2

Binding of Anti-CRP Antibodies to a Polymer According to the Invention

An antiserum was obtained by immunization of rabbits with purified C-reactive protein (CRP). The gamma-globulin fraction was obtained from this by an ion-exchange method using DE-32 cellulose. This fraction was employed with a protein content of about 10 mg/ml.

3.22 ml of the polymer described in Example 1 were mixed with 0.1 ml of anti-CRP antibody solution. Then 0.05 ml of a 20 g/100 ml aqueous solution of eicosoxyethylene sorbitan laurate (®Tween 20) was added, followed by renewed mixing. To this mixture was added 0.05 ml of 1 N HCl so that a pH of about 2 was reached.

After an incubation time of 30 minutes at room temperature, 0.25 ml of saturated aqueous disodium hydrogen phosphate solution (pH 6.5) and 0.25 ml of sodium cyanoborohydride (25 mg/ml) were added, followed by thorough mixing.

An incubation at room temperatures was subsequently carried out for one hour. This loading mixture was then centrifuged at about 50,000 × for 30 minutes (Beckman centrifuge, 20,000 rpm). The supernatant was discarded. The residue was resuspended in 2 ml of glycine/NaCl buffer (0.1 M glycine, 0.17 M NaCl, 0.5 g/100 ml eicosoxyethylene sorbitan laurate (®Tween 20) pH 8.2).

An ultrasonic treatment (Bronson Sonyfier B 15) was subsequently carried out for 2 seconds. The reagent redispersed in this way was diluted in the ratio by volume 1:40 with 0.025 M imidazole buffer pH 8.2 (3 g/100 ml sucrose, 0.05 g/100 ml human albumin, 0.05 g/100 ml NaN$_3$).

EXAMPLE 3

Turbidimetric Measurement of CRP Concentrations in Serum Samples

The CRP reagent prepared as in Example 2 by binding anti-CRP antibodies to polymers according to the invention was employed to measure CRP in patients' sera.

The standard used was a CRP standard serum with a CRP concentration of 26 mg/l (Behringwerke AG). The standard was diluted 1:10, 1:20, 1:40, 1:80, 1:160 and 1:320 with physiological saline. The patients' sera were diluted 1:100 with physiological saline.

For the measurement, 80 μl of patient's serum dilution or standard serum dilution were mixed with 450 μl of a reaction buffer (0.1 M glycine, 0.17 M NaCl, 4 g/100 ml polyethylene glycol 6,000, 0.5 g/100 ml ®Tween 20, pH 8.2) and 150 μl of CRP reagent from Example 2 in microcuvettes (1×0.4 cm, from Sarstedt). The extinction at a wavelength of 334 nm for the cuvettes was then measured in an Eppendorf photometer after 10 seconds and after 3 minutes. The measurements were calculated as the difference between the values at 10 seconds and at 3 minutes.

The reference plot for the measurement of the standard was drawn on semilogarithmic paper with concentrations on the abscissa and the extinctions on the ordinate, and the measurements for the patients' sera were evaluated thereon.

EXAMPLE 4

Binding of anti-IgE antibodies to a polymer according to the invention from Example 1

An antiserum was obtained by immunization of rabbits with purified immunoglobulin E (IgE). The antibody was obtained from this by an immunoadsorption method using carrier-bound IgE. It was subsequently concentrated to a protein content of about 10 mg/ml.

5.64 ml of the polymer prepared as in Example 1 were mixed with 0.1 ml of anti-IgE antibody solution.

Then 0.05 ml of an aqueous solution containing 20 g/100 ml eicosoxyethylene sorbitan laurate (®Tween 20) was added, followed by renewed mixing. 0.18 ml of 1 N HCl was added to this so that a pH of about 2 was reached. After an incubation time of 30 minutes at room temperature, 0.25 ml of a saturated aqueous disodium hydrogen phosphate solution (pH 6.5) and 0.25 ml of sodium cyanoborohydride (25 mg/ml) were added, followed by thorough mixing. An incubation at room temperature was subsequently carried out for one hour. This loading mixture was then centrifuged at about 50,000 × g for 30 minutes (Beckman centrifuge, 20,000 rpm). The supernatant was discarded. The residue was resuspended in 2 ml of glycine/NaCl buffer (0.1 M glycine, 0.17 M NaCl, 0.5 g/100 ml eicosoxyethylene sorbitan laurate pH 8.2). An ultrasonic treatment (Bronson Sonyfier B 15) was subsequently carried out for 2 seconds. The reagent redispersed in this way was diluted in the ratio by volume 1:20 with 0.025 M imidazole buffer pH 8.2 (3 g/100 ml sucrose, 0.05 g/100 ml human albumin, 0.05 g/100 ml NaN$_3$).

EXAMPLE 5

Turbidimetric Measurement of IgE Concentrations in Serum Samples

The reagent for the determination of IgE prepared as in Example 4 by binding anti-IgE antibodies to latex preparations according to the invention was employed to measure IgE in patients' sera.

The standard used was an IgE standard serum with an IgE concentration of 433 IU/ml (from Behringwerke AG). The standard was additionally diluted 1:2, 1:4, 1:8, 1:16, 1:32 and 1:64 with physiological saline. The patients' sera were diluted 1:5 with physiological saline. For the measurement, 80 μl of patient's serum dilution or standard serum dilution were mixed with 450 μl of a reaction buffer (0.1 M glycine, 0.17 M NaCl, 4 g/100 ml polyethylene glycol 6000, 0.5 g/100 ml ®Tween 20, pH 8.2) and 40 μl of a solution of rabbit serum diluted 1:32 in NaCl solution containing 6 g/100 ml and 4 g/100 ml ®Tween 20, as well as 150 μl of IgE reagent from Example 4, in microcuvettes (1×0.4 cm, from Sarstedt). The extinction at a wavelength of 334 nm for the cuvettes was then measured in an Eppendorf photometer after 10 seconds and after 3 minutes. The measurements were calculated as the difference between the values at 10 seconds and at 3 minutes.

The reference plot for the measurement of the standard was drawn on semilogarithmic paper with IgE concentrations on the abscissa and the extinctions on the ordinate, and the measurements for the patients' sera were evaluated thereon.

EXAMPLE 6

Binding of Anti AFP Antibodies to a Polymer According to the Invention

An antiserum was obtained by immunization of rabbits with purified alpha-fetoprotein (AFP). The antibody was obtained from this by an immunoadsorption method using carrier-bound AFP. It was subsequently concentrated to a protein content of about 10 mg/ml.

5.64 ml of the polymer prepared as in Example 1 were mixed with 0.1 ml of anti-AFP antibody solution.

Then 0.05 ml of a 20 g/100ml aqueous solution of eicosoxyethylene sorbitan laurate (®Tween 20) was added, followed by renewed mixing. To this mixture was added 0.18 ml of 1 N HCl so that a pH of about 2 was reached. After an incubation time of 30 minutes at room temperature, 0.25 ml of a saturated aqueous disodium hydrogen phosphate solution (pH 6.5) and 0.25 ml of sodium cyanoborohydride (25 mg/ml) were added, followed by thorough mixing. An incubation at room temperatures was subsequently carried out for one hour.

This laoding mixture was then centrifuged at about 50,000 × g for 30 minutes (Beckham centrifuge, 20,000 rpm).

The supernatant was discarded. The residue was resuspended in 2 ml of glycine/NaCl buffer (0.1 M glycine, 0.17 MNaCl, 0.5 g/100 ml (®Tween 20 pH 8.2).

An ultrasonic treatment (Bronson Sonyfier B 15) was subsequently carried out for 2 seconds. The reagent redispersed in this way was diluted in the ratio by volume 1:40 with 0.025 M imidazole buffer pH 8.2 (3 g/100 ml sucrose, 0.05 g/100 ml human albumin, 0.05 g/100 ml NaN₃).

EXAMPLE 7

Turbidimetric Measurement of AFP Concentrations in Serum Samples

The reagent for the determination of AFP prepared as in Example 6 by binding anti-AFP antibodies to latex preparations according to the invention (from Example 1) was employed to measure AFP in patients' sera.

The standard used was an AFP standard serum with an AFP concentration of 300,000 ng/ml (from Behringwerke AG).

The standard was diluted stepwise to 600 ng/ml in an AFP-free pooled serum. This dilution was used to prepare a standard series with decreasing AFP concentrations in the dilutions 1:2, 1:4, 1:8, 1:16, 1:32 and 1:64 with physiological saline. The patients' sera were diluted 1:5 with physiological saline.

For the measurement, 80 μl of patient's serum dilution or standard serum dilution were mixed with 450 μl of a reaction buffer (0.1 M glycine, 0.17 M NaCl, 4 g/100 ml polyethylene glycol 6,000, 0.5 g/100 ml ®Tween 20, pH 8.2) and 10 μl of a solution of rabbit serum diluted 1:8 in a solution-containing 8 g/100 ml NaCl and 5 g/100 ml ®Tween 20 , as well as with 150 μl of AFP reagent from Example 6, in microcuvettes (1×0.4 cm, from Sarstedt). The extinction at a wavelength of 334 nm for the cuvettes was then measured in an Eppendorf photometer after 10 seconds and after 3 minutes. The measurements were calculated as the difference between the values at 10 seconds and at 3 minutes.

The reference plot for the measurement of the standard was drawn on semilogarithmic paper with concentrations on the abscissa and the extinctions on the ordinate, and the measurements for the patients' sera were evaluated thereon.

We claim:

1. A latex containing substantially homogeneous latex particles comprising at least one acetal group containing monomer of the formula I

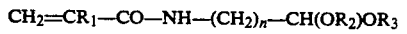

$$CH_2=CR_1-CO-NH-(CH_2)_n-CH(OR_2)OR_3 \quad I$$

in which n is 1-6, and

R₁ is H or CH₃ and R₂ and R₃ are identical or different and are —(CH₂)ₘ—CH₃ with m being 0-7 or —C(X)(Y)Z with X, Y and Z being (CH₂)ₚCH₃, and p being 1-3, where X, Y, and Z can be identical or different.

2. A process for the preparation of a latex containing substantially homogeneous latex particles which consists essentially of copolymerizing (a) at least one acetal group containing monomer of the formula I

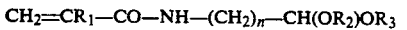

$$CH_2=CR_1-CO-NH-(CH_2)_n-CH(OR_2)OR_3 \quad I$$

in which n is 1-6, and

R₁ is H or CH₃ and R₂ and R₃ are identical or different and are —(CH₂)ₘ—CH₃ with m being 0-7 or —C(X)(Y)Z with X, Y and Z being (CH₂)ₚCH₃, and p being 1-3, where X, Y, and Z can be identical or different and, (b) at least one additional vinyl monomer in an aqueous medium in the presence of an emulsifier and of a radical-forming initiator.

3. A latex containing substantially homogeneous latex particles as claimed in claim 1, wherein the acetal group containing monomer is selected from the group consisting of acrylamidoacetaldehyde dialkyl acetal in which the alkyl groups have from 2 to 8 carbon atoms and methacrylamidoacetaldehyde dialkyl acetal in which the alkyl group shave from 2 to 8 carbon atoms.

4. A latex containing substantially homogeneous latex particles as claimed in claim 1, wherein the acetal group containing monomer is selected from the group consisting of acrylamidoacetaldehyde di-n-pentyl acetal and methacrylamidoacetaldehyde di-n-pentyl acetal.

5. A latex containing substantially homogeneous latex particles as claimed in claim 1, wherein said latex particles comprise a copolymer of:

(a) at least one monomer of the formula I

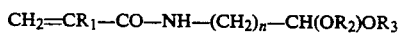

$$CH_2=CR_1-CO-NH-(CH_2)_n-CH(OR_2)OR_3 \quad I$$

and, (b) at least one other vinyl monomer.

6. A latex containing substantially homogeneous latex particles as claimed in claim 5, wherein said at least one other vinyl monomer is selected from the group consisting of styrene, vinylnaphtalene, vinyltoluene, methacrylic acid, acrylic acid and crotonic acid.

7. A latex containing substantially homogeneous latex particles as claimed in claim 5, wherein said at least one other vinyl monomer is selected from the group of water-soluble monomers consisting of hydroxyl-substituted acrylic esters, hydroxyl-substituted methacrylic esters, hydroxyl-substituted acrylic amides, hydroxyl-substituted methacrylic amides, and water-soluble monomers with a betaine structure.

8. A latex containing latex particles consisting essentially of a copolymer of;

(a) at least one acetal group containing monomer of the formula I

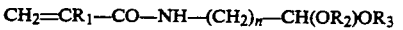

$$CH_2=CR_1-CO-NH-(CH_2)_n-CH(OR_2)OR_3 \quad I$$

in which n is 1-6, and

R₁ is H or CH₃ and R₂ and R₃ are identical or different and are —(CH₂)ₘ—CH₃ with m being 0-7 or —C(X)(Y)Z with X, Y and Z being (CH₂)ₚCH₃, and p being 1-3, where X, Y, and Z can be identical or different and, (b) at least one other vinyl monomer.

9. A latex containing latex particles as claimed in claim 8, wherein the acetal group containing monomer is selected from the group consisting of acrylamidoacetaldehyde dialkyl acetal in which the alkyl groups have from 2 to 8 carbon atoms and methacrylamidoacetaldehyde dialkyl acetal in which the alkyl groups have from 2 to 8 carbon atoms.

10. A latex containing latex particles as claimed in claim 8, wherein the acetal group containing monomer is selected from the group consisting of acrylamidoacetaldehyde di-n-pentyl acetal and methacrylamidedoacetaldehyde di-n-pentyl acetal.

11. A latex containing latex particles as claimed in claim 8, wherein said at least one other vinyl monomer is selected from the group consisting of styrene, vinylnaphthalene, vinyltoluene, methacrylic acid, acrylic acid and crotonic acid.

12. A latex containing latex particles as claimed in claim 8, wherein said at least one other vinyl monomer is selected from the group consisting of N-(2,3-dihydroxypropyl)methacrylamide, N-(2-hydroxypropyl)methacrylamide, 2-hydroxypropyl methacrylate, N-(3-sulfopropyl)-N-methacryloxyethyl-N,N-dimethylammonium betaine and N-(3-sulfopropyl)-N-methacrylamidopropyl-N,-N-dimethylammonium betaine.

13. A latex containing latex particles as claimed in claim 8, wherein said latex particles are prepared directly by the copolymerization of the at least one acetal group containing monomer and the at least one other vinyl monomer.

* * * * *